(12) United States Patent
Dierking et al.

(10) Patent No.: US 8,696,739 B2
(45) Date of Patent: Apr. 15, 2014

(54) BARBED ANCHOR

(75) Inventors: William Kurt Dierking, Louisville, KY (US); Carl Agnew, West Lafayette, IN (US); Shuo Yang, West Lafayette, IN (US); Blayne A. Roeder, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 197 days.

(21) Appl. No.: 13/357,243

(22) Filed: Jan. 24, 2012

(65) Prior Publication Data

US 2013/0023981 A1    Jan. 24, 2013

Related U.S. Application Data

(63) Continuation-in-part of application No. 12/360,638, filed on Jan. 27, 2009, now Pat. No. 8,394,139.

(60) Provisional application No. 61/093,172, filed on Aug. 29, 2008, provisional application No. 61/437,343, filed on Jan. 28, 2011.

(51) Int. Cl.
*A61F 2/06* (2013.01)

(52) U.S. Cl.
USPC ........ 623/1.36; 623/1.15; 623/1.32; 623/1.35

(58) Field of Classification Search
USPC ............................ 623/1.15, 1.32, 1.35, 1.36
See application file for complete search history.

(56) References Cited

U.S. PATENT DOCUMENTS

| | | | | |
|---|---|---|---|---|
| 5,902,334 A | * | 5/1999 | Dwyer et al. | 606/194 |
| 5,921,995 A | * | 7/1999 | Kleshinski | 606/153 |
| 6,203,568 B1 | | 3/2001 | Lombardi et al. | |
| 6,517,573 B1 | * | 2/2003 | Pollock et al. | 623/1.15 |
| 6,860,901 B1 | * | 3/2005 | Baker et al. | 623/1.36 |
| 7,572,289 B2 | | 8/2009 | Sisken et al. | |
| 7,766,954 B2 | * | 8/2010 | Chobotov et al. | 623/1.13 |
| 8,048,140 B2 | * | 11/2011 | Purdy | 623/1.13 |
| 8,372,142 B2 | * | 2/2013 | Majercak et al. | 623/1.36 |
| 2003/0120331 A1 | | 6/2003 | Chobotov et al. | |
| 2003/0120338 A1 | * | 6/2003 | Chobotov et al. | 623/1.36 |

(Continued)

FOREIGN PATENT DOCUMENTS

| | | |
|---|---|---|
| EP | 0 701 800 A1 | 3/1996 |
| WO | WO 00/35352 A1 | 6/2000 |

OTHER PUBLICATIONS

International Search Report for EP 12152911.9, dated Jun. 20, 2012, 7 pages.

*Primary Examiner* — Thomas J Sweet
*Assistant Examiner* — Seema Mathew
(74) *Attorney, Agent, or Firm* — Brink Gilson & Lione (57) ABSTRACT

An endoluminal prosthesis includes a support structure including a curvilinear portion having a first strut and a second strut that meet at an apex. Disposed on the support structure is an anchor with an anchor body and one or more barbs extending outwardly from the anchor body. The anchor body can fit at least partially about, and can conform to the first strut, second strut, and the apex. A curved portion of the anchor and the curvilinear portion of the support structure can be co-formed, resulting in a secure interference fit so that welding, soldering, or other joining mechanisms can be avoided. Cutouts can be formed along the curved portion of the anchor to relieve stress or strain during the co-forming process.

14 Claims, 11 Drawing Sheets

(56) References Cited

U.S. PATENT DOCUMENTS

| | | |
|---|---|---|
| 2003/0144688 A1 | 7/2003 | Brady et al. |
| 2003/0158604 A1 | 8/2003 | Cauthen, III et al. |
| 2003/0236570 A1* | 12/2003 | Cook et al. ............... 623/1.36 |
| 2004/0117004 A1 | 6/2004 | Osborne et al. |
| 2004/0186561 A1* | 9/2004 | McGuckin et al. ......... 623/1.36 |
| 2004/0220595 A1 | 11/2004 | Frazier et al. |
| 2004/0250595 A1* | 12/2004 | Cronholm et al. ............ 72/350 |
| 2005/0070993 A1 | 3/2005 | Boekstegers et al. |
| 2005/0080480 A1 | 4/2005 | Bolea et al. |
| 2005/0240259 A1 | 10/2005 | Sisken et al. |
| 2006/0025850 A1* | 2/2006 | Feller et al. ............... 623/1.16 |
| 2006/0122684 A1* | 6/2006 | Lye et al. .................. 623/1.2 |
| 2007/0055363 A1* | 3/2007 | Chuter et al. ............. 623/1.35 |
| 2008/0033534 A1* | 2/2008 | Cook et al. ............... 623/1.36 |
| 2008/0208329 A1* | 8/2008 | Bishop et al. ............. 623/2.11 |
| 2009/0149946 A1 | 6/2009 | Dixon ..................... 623/1.36 |
| 2010/0016953 A1 | 1/2010 | Sisken et al. |
| 2010/0057195 A1 | 3/2010 | Roeder et al. |
| 2012/0095547 A1* | 4/2012 | Chuter ..................... 623/1.35 |
| 2012/0130470 A1* | 5/2012 | Agnew et al. ............. 623/1.11 |
| 2013/0073029 A1* | 3/2013 | Shaw ....................... 623/1.36 |

* cited by examiner

BARBED ANCHOR

RELATED APPLICATIONS

The present patent document is a continuation in part under 35 U.S.C. §120 of U.S. patent application Ser. No. 12/360,638, now U.S. Pat. No. 8,394,139 filed Jan. 27, 2009 which claims the benefit of the filing date under 35 U.S.C. §119(e) of U.S. Patent Application Ser. No. 61/093,172, filed Aug. 29, 2008, and claims the benefit of the filing date under 35 U.S.C §119(e) of U.S. Patent Application Ser. No. 61/437,343, filed Jan. 28, 2011, which is hereby incorporated by reference in its entirety.

TECHNICAL FIELD

The present invention relates to an attachable anchor with a barb for use on a medical device such as a prosthesis and a method of attaching an anchor onto a medical device.

BACKGROUND

Barbs attached to stents help secure placement of a stent graft in a treated vasculature. Proper stent attachment and placement of the barb ensures that the stent graft will stay in place for the lifespan of the stent graft. Some stent designs limit the barb attachment location and method of attachment due to the material used in the barb and stent and due to the material used to attach the two. Other factors may also limit the barb attachment location, including strut crossover during crimping or potential stent fatigue failure due to weld location near a region on the wire stent of high stress or strain.

Some methods of attaching barbs to wire stents include silver soldering the barb to the wire stent, laser cutting the barb directly into a cannula-cut stent design, and laser welding a barb to the strut of the wire stent. Each of these methods may present particular limitations to barb placement and barb fatigue life depending on the stent design. In particular, welding or soldering a barb to a stent wire not only introduces an additional step in the manufacturing of a prosthesis such as a stent graft, but also introduces stress risers at locations where the welding heat is applied. The industry would benefit from expanded capabilities in barb attachment methods.

What is needed is a simplified barbed anchor that can be easy to manufacture, readily and securely attachable to a prosthesis, preferably by interference fit, and produce predictable results with respect to fatigue life and ability to anchor the prosthesis at the site of deployment.

BRIEF SUMMARY

The foregoing problems are solved and a technical advance is achieved with an anchor that is configured for attachment to an endoluminal prosthesis. The endoluminal prosthesis can include a support structure having a curvilinear portion. The curvilinear portion can have a first straight section and a second straight section that meet at a curved apex segment.

The anchor can include a tubular body and one or more barbs extending outwardly from the tubular body. The anchor can have a first anchor segment configured to fit about the first straight segment of the support structure, a second anchor segment configured to fit about the second straight segment, and a third curved anchor segment disposed between the first and second anchor segments and configured to fit about and conform to the curved apex segment of the support structure. Relief cutouts can be provided along the curved third segment to facilitate formation of the curved segment of the support structure and protect the structural integrity of the plastically deformed anchor during bending. In some examples, the anchor can have one or more complete ring segments to prevent premature breaking off or dislodgement of the anchor from the support structure. In one aspect, the anchor can be directly fixed to the support structure with a secure mechanical interference fit.

Further provided is a method of attaching an anchor to an endoluminal support structure. The anchor can have a tubular body with one or more barbs, having a first configuration prior to bending. A strut member that is in a first configuration prior to bending can be inserted into a lumen of the anchor in the first configuration, and positioned at a bending site. The strut member and the anchor together can be bent at the bending site, preferably simultaneously bent together at the bending site. To this end, the strut has a bent second configuration with a curvilinear portion including a first straight segment, a second straight segment, and a curved segment between the first and second straight segments. The anchor has a bent second configuration, which can be a curvilinear shape, V-shaped, or U-shaped, with a first anchor segment fitted about the first straight segment, a second anchor segment fitted about the second straight segment, and a third curved anchor segment fitted and conformed about the curved apex segment of the strut. The anchor can be directly fixed to the strut with a secure mechanical interference fit. Preferably, the anchor is fixed to the support structure without the use of additional steps or materials from joining mechanisms such as welding, soldering, adhesives or the like.

BRIEF DESCRIPTION OF THE DRAWINGS

FIG. 1b is a perspective view of an anchor made from a stamped out sheet shown in FIG. 1a.

FIG. 9b is a side profile view of the anchor in FIG. 9a.

FIG. 9c is an end profile view of the anchor in FIG. 9a.

FIG. 10b is an end profile view of the anchor in FIG. 10a.

FIG. 11b is a front view of the anchor in FIG. 11a.

DETAILED DESCRIPTION OF THE DRAWINGS AND THE PRESENTLY PREFERRED EMBODIMENTS

The term "prosthesis" means any replacement for a body part or for a function of that body part or any device that enhances or adds functionality to a physiological system.

The term "support structure" means any device that is attached to a prosthesis. For example, a support structure can comprise stents, radiopaque markers, anchoring stents, barbs, and lateral support rings for supporting a fenestration. The structural components can be attached to the exterior of the graft, the interior of the graft, and/or can be sandwiched between two or more layers of graft material.

The support structure can be made from numerous base materials, such as: biocompatible metals or other metallic materials; polymers including bioabsorbable or biostable polymers; stainless steels; nickel-titanium alloys including shape memory or superelastic types (e.g., nitinol or elastinite); noble metals including platinum, gold, or palladium; refractory metals including tantalum, tungsten, molybdenum, or rhenium; stainless steels alloyed with noble and/or refractory metals; silver; rhodium; inconel; iridium; niobium; titanium; magnesium; amorphous metals; plastically deformable metals (e.g., tantalum); nickel-based alloys (e.g., including platinum, gold, and/or tantalum alloys); iron-based alloys (e.g., including platinum, gold, and/or tantalum alloys); cobalt-based alloys (e.g., including platinum, gold, and/or tantalum alloys); cobalt-chrome alloys (e.g., elgiloy); cobalt-chromium-nickel alloys (e.g., phynox); alloys of cobalt, nickel, chromium, and molybdenum; cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; nonmetallic biocompatible materials including polyamides, polyolefins (e.g., polypropylene or polyethylene), nonabsorbable polyesters (e.g., polyethylene terephthalate), or bioabsorbable aliphatic polyesters (e.g., homopolymers or copolymers of lactic acid, glycolic acid, lactide, glycolide, para-dioxanone, trimethylene carbonate or c-caprolactone); polymeric materials (e.g., poly-L-lactic acid, polycarbonate, polyethylene terephthalate, or engineering plastics such as thermotropic liquid crystal polymers (LCPs)); biocompatible polymeric materials (e.g., cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene, or polytetrafluoroethylene); degradable or biodegradable polymers, plastics, natural (e.g., animal, plant, or microbial) or recombinant material (e.g., polylactic acid, polyglycolic acid, polyanhydride, polycaprolactone, polyhydroxybutyrate valerate, polydepsipeptides, nylon copolymides, conventional poly (amino acid) synthetic polymers, pseudo-poly(amino acids), or aliphatic polyesters (e.g., polyglycolic acid (PGA), polylactic acid (PLA), polyalkylene succinates, polyhydroxybutyrate (PHB), polybutylene diglycolate, poly epsilon-caprolactone (PCL), polydihydropyrans, polyphosphazenes, polyorthoesters, polycyanoacrylates, polyanhydrides, polyketals, polyacetals, poly($\alpha$-hydroxy-esters), poly(carbonates), poly(imino-carbonates), poly($\beta$-hydroxy-esters), or polypeptides)); polyethylene terephthalate (e.g., Dacron® or Mylar®); expanded fluoropolymers (e.g., polytetrafluoroethylene (PTFE)); fluorinated ethylene propylene (FEP); copolymers of tetrafluoroethylene (TFE) and per fluoro(propyl vinyl ether) (PFA)); homopolymers of polychlorotrifluoroethylene (PCTFE) and copolymers with TFE; ethylene-chlorotrifluoroethylene (ECTFE); copolymers of ethylene-tetrafluoroethylene (ETFE); polyvinylidene fluoride (PVDF); polyvinyfluoride (PVF); polyaramids (e.g., Kevlar®); polyfluorocarbons including polytetrafluoroethylene with and without copolymerized hexafluoropropylene (e.g., Teflon® or Goretex®); expanded fluorocarbon polymers; polyglycolides; polylactides; polyglycerol sebacate; polyethylene oxide; polybutylene terepthalate; polydioxanones; proteoglymays; glycosaminoglymays; poly(alkylene oxalates); polyalkanotes; polyamides; polyaspartimic acid; polyglutarunic acid polymer; poly-p-diaxanone (e.g., PDS); polyphosphazene; polyurethane including porous or nonporous polyurethanes; poly(glycolide-trimethylene carbonate); terpolymer (copolymers of glycolide, lactide, or dimethyltrimethylene carbonate); polyhydroxyalkanoates (PHA); polyhydroxybutyrate (PHB) or poly(hydroxybutyrate-co-valerate) (PHB-co-HV); poly(epsilon-caprolactone) (e.g., lactide or glycolide); poly(epsilon-caprolactone-dimethyltrimethylene carbonate); polyglycolic acid (PGA); poly-L and poly-D(lactic acid) (e.g., calcium phosphate glass); lactic acid/ethylene glycol copolymers; polyarylates (L-tyrosine-derived) or free acid polyarylates; polycarbonates (tyrosine or L-tyrosine-derived); poly(ester-amides); poly(propylene fumarate-co-ethylene glycol) copolymer (e.g., fumarate anhydrides); polyanhydride esters; polyanhydrides; polyorthoesters; prolastin or silk-elastin polymers (SELP); calcium phosphate (bioglass); compositions of PLA, PCL, PGA ester; polyphosphazenes; polyamino acids; polysaccharides; polyhydroxyalkanoate polymers; various plastic materials; Teflon®); nylon; block polymers or copolymers; Leica RM2165; Leica RM2155; organic fabrics; biologic agents (e.g., protein, extracellular matrix component, collagen, fibrin); small intestinal submucosa (SIS) (e.g., vacuum formed SIS); collagen or collagen matrices with growth modulators; aliginate; cellulose and ester; dextran; elastin; fibrin; gelatin; hyaluronic acid; hydroxyapatite; polypeptides; proteins; ceramics (e.g., silicon nitride, silicon carbide, zirconia or alumina); bioactive silica-based materials; carbon or carbon fiber; cotton; silk; spider silk; chitin; chitosan (NOCC or NOOC-G); urethanes; glass; silica; sapphire; composites; any mixture, blend, alloy, copolymer or combination of any of these; or various other materials not limited by these examples.

The term "stent" means any device that provides rigidity, expansion force, or support to a prosthesis, such as a stent graft. In one configuration, the stent can represent a plurality of discontinuous devices. In another configuration, the stent can represent one device. Stents can have a wide variety of configurations and can be balloon-expandable or self-expanding. Typically, stents have a circular cross-section when fully expanded, so as to conform to the generally circular cross-section of a body lumen. In one example, a stent can comprise struts (elongate portions) and acute bends (curvilinear portions) that are arranged in a zigzag configuration, as exemplified in a Z-stent that is commercially available from Cook Incorporated (Bloomington, Ind.), in which the struts are set at angles to each other and are connected by the acute bends.

A variety of biocompatible materials can be employed to construct the stent, or portions of the stent, including metals and/or alloys, medically-acceptable polymers and/or bioabsorbable polymers, or materials. The metals and/or alloys may, among other things, include stainless steel, tantalum, nitinol, gold, silver, tungsten, platinum, inconel, cobalt-chromium alloys, and iridium, all of which are commercially available metals or alloys used in the fabrication of medical devices. In a preferred configuration, the stent is constructed from nitinol, stainless steel, and/or cobalt-chromium alloys.

The anchors having barbs described herein can be in one piece, or monolithic, or have multiple wires in a multi-filar configuration to form a tube. The monolithic anchors can be stamped, machined, or laser cut out of a sheet or cannula of biocompatible material. The multi-filar anchors can be provided with wires having circular or polygonal cross-sections by methods used in the art.

Figure 1A:
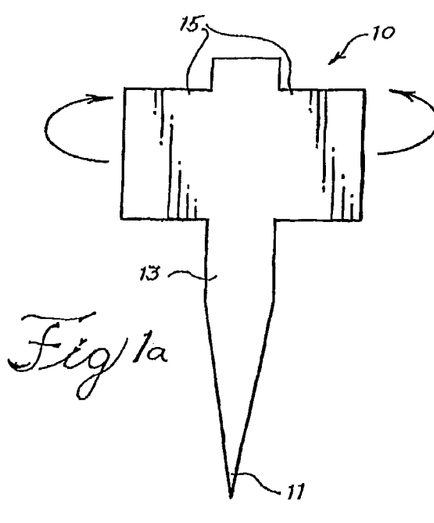
FIG. 1a is a top view of a stamped out sheet of biocompatible material for use as an anchor with two winged portions.
Figure 1B:
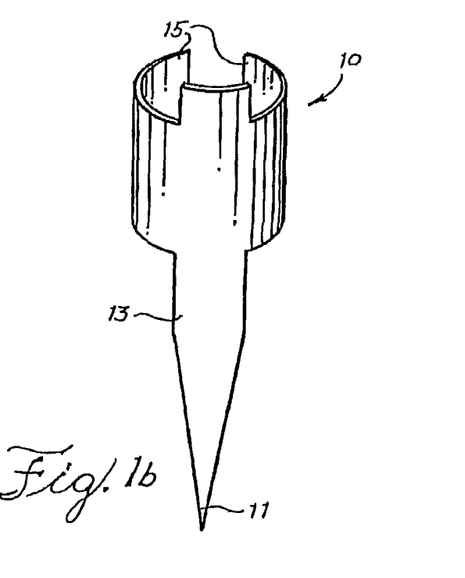
Figure 1C:
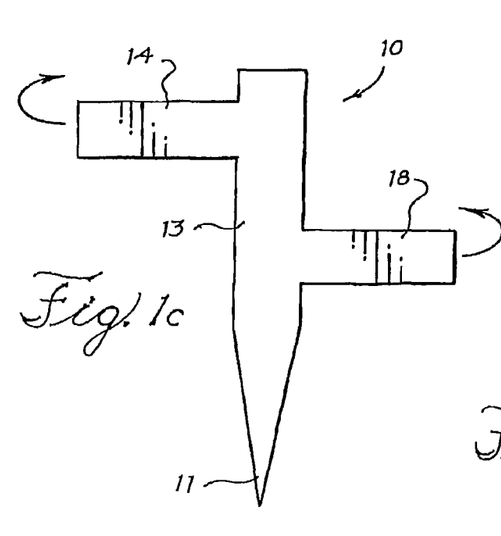
FIG. 1c is a top view of a stamped out sheet of biocompatible material with opposing and off-setting winged segments.
Figure 1D:
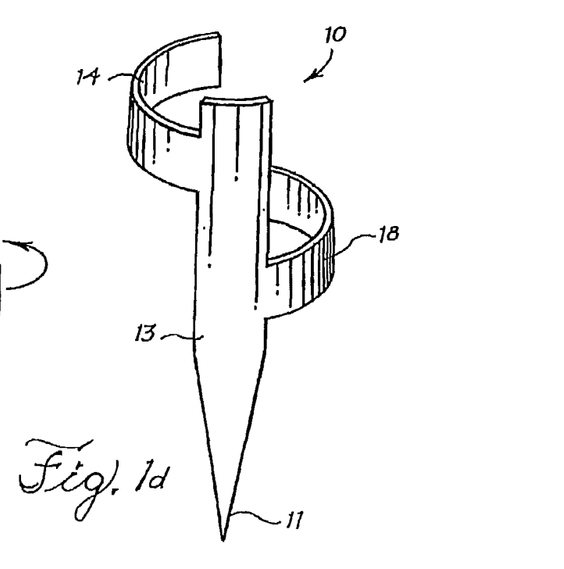
FIG. 1d is a perspective view of an anchor made from the stamped out sheet shown in FIG. 1c.

In FIGS. 1a, 1b, 1c, 1d, 1e, and 1f the anchor is monolithically constructed. The anchor 10 can include a longitudinal body 13 having a barb 11 at one end and first and second substantially opposing curved portions 15 disposed along the length of, and perpendicular to the longitudinal body 13. In FIGS. 1a-b, the anchor 10 has two substantially opposing portions 15 perpendicular to the longitudinal body 13. These portions 15 will be shaped to fit about and to conform to a strut. In FIG. 1c-d, an anchor is shown having more than two opposing portion where there is a first curved portion 14 that is longitudinally offset from the second curved portion 18. The curved portions can be configured for fastening the anchor 10 to the stent by snap fitting the curved portions around a strut or, if necessary, soldering the curved portion to the strut. The anchor also can include a longitudinal body 13 with more than one barb 11. The barb can be forked at the end to provide two or three separate prongs.

The straight portions 15 shown in FIG. 1a are bent in the direction shown by the arrows to provide the two curved portions 15 shown in FIG. 1b. FIG. 1c shows a monolithic anchor 10 with two substantially opposing portions 14, 18 that are longitudinally offset to one another. As shown in FIG. 1d, these portions 14, 18 are manipulated in the direction shown by the arrows to provide two curved portions 14, 18 that conform to the tubular elongate portion of a stent strut.

Figure 1E:
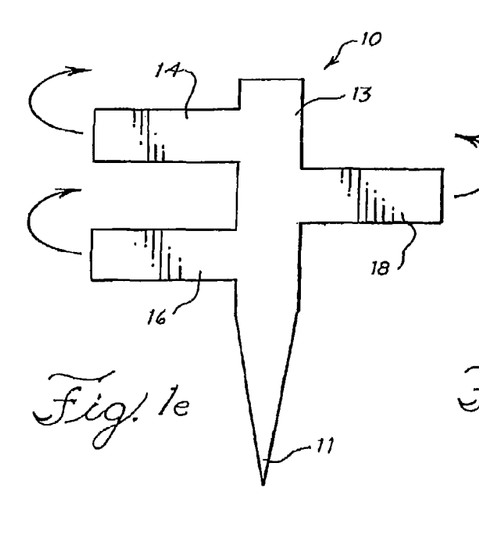
FIG. 1e is a top view of a stamped out sheet of biocompatible material with two winged segments opposed to one winged segment.
Figure 1F:
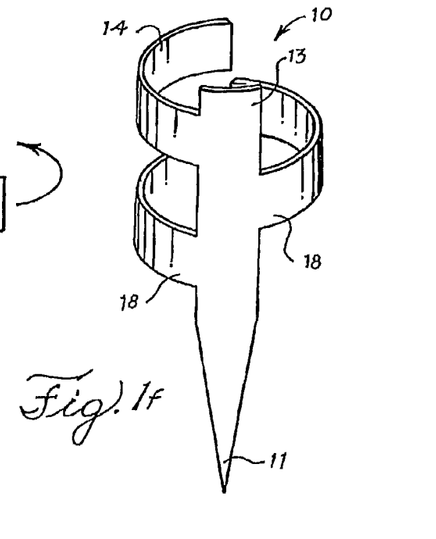
FIG. 1f is a perspective view of an anchor made from the stamped out sheet shown in FIG. 1e.

FIG. 1e also shows an anchor 10 formed out of a sheet of biocompatible material. Three portions 14, 16, 18 are bent in the direction shown by the arrows to provide the curved portions 14, 16, 18 shown in FIG. 1f. Curved portions 14, 16, 18 are disposed along the length of and are perpendicular to the longitudinal body 13. Curved portion 18 is longitudinally offset from curved portions 14, 16. An anchor can be made having more than one, two, or even three curved portions where some of the curved portions are opposed to the remainder. The number of curved portions and their configuration can vary. Positioning the curved portions in opposing configurations facilitates the stable attachment of the anchor to the strut of the stent.

Figure 2:
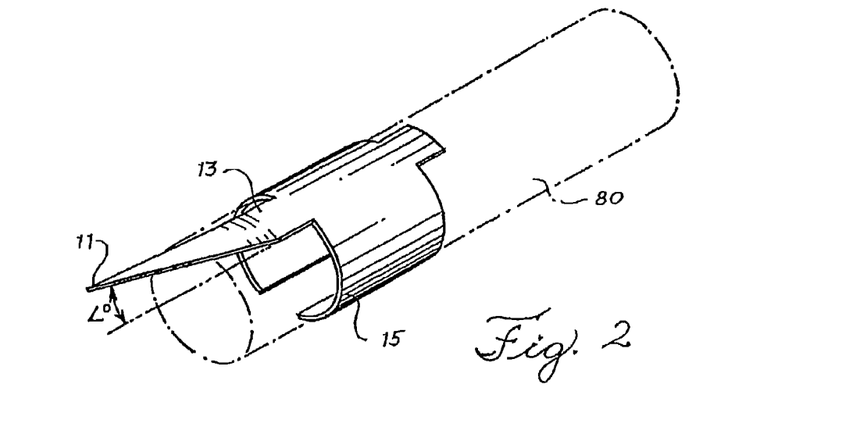
FIG. 2 is a perspective view of an anchor fastened to a stent strut.
Figure 3A:
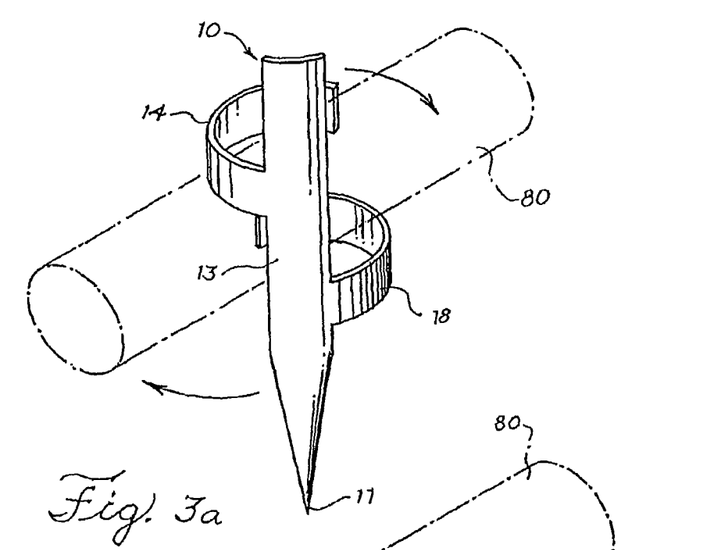
FIGS. 3a and 3b depict the steps to fasten a monolithic anchor to a stent strut.
Figure 3B:
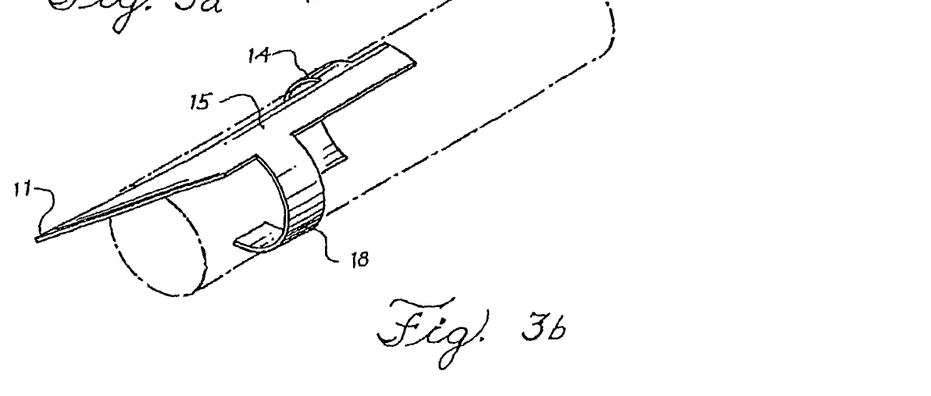

The anchor 10 also includes a barb 11 that, when the prosthesis is implanted into a vasculature, assists in securing the anchor and the stent graft to the vessel wall or to the wall of a mating graft. The barb 11 can be parallel to the elongate portion of a stent strut 80, extend from the elongate portion at an angle away from the strut 80, as shown in FIG. 2, or bent towards the strut 80. The barb 11 in FIG. 3b is in line with the stent elongate portion 80.

Figures 5A, 5B:
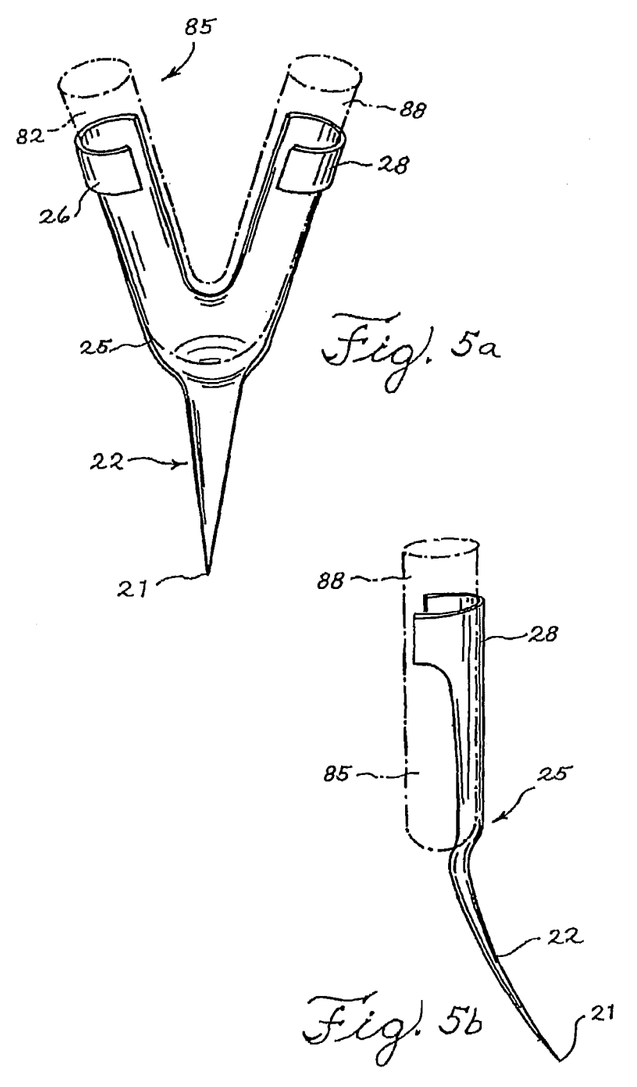
FIG. 5a is a perspective view of a monolithic anchor with a bifurcated attachment end fastened to a curvilinear portion of a stent strut.
FIG. 5b is a profile view of a monolithic anchor with a bifurcated attachment end fastened to a curvilinear portion of a stent strut.

The anchor 10 can have geometries permitting press-fit or snap-on placement of the anchor 10 onto a stent strut at either an elongate portion 80 or at the curvilinear portion 85, or apex, of a Z-stent, as shown in FIG. 5a. A sheet of an appropriate material, such as an alloy, can be stamped to incorporate curved and linear segments that act to fasten the anchor 10 around the stent strut 80 and hold the anchor 10 in place. FIG. 2 shows an anchor 10 fastened to the elongate portion 80 of a stent. FIG. 5a shows an anchor 20 fastened to the curvilinear portion 85 of a stent. As shown in FIG. 5a, the two clamping portions 26, 28 of the anchor substantially mimic and conform to the curvilinear portion 85 of the stent. The clamping portions 26, 28 of the anchor 10 then can support the resultant forces and moments through the points of contact between the stent and the anchor 10 without the need for solder, welding, glue, or epoxy.

There is a method of attaching an anchor 10 to an endoluminal support structure that has an elongate strut 80. FIGS. 3a and 3b are illustrations of steps that can be taken to fasten a monolithic anchor 10 having two offset curved portions 14, 18 to the elongate strut 80. The two curved portions 14, 18 are offset and opposed to one another and are bent to fit around the stent elongate portion 80. To fasten the anchor 10 onto the stent elongate portion 80 the, the longitudinal body 13 part of the anchor 10 is initially placed perpendicular to the stent elongate portion 80 such that the elongate portion 80 lies between the curved portions 14, 18. The anchor 10 can then be rotated in a clockwise direction as shown by the arrows in FIG. 3a to fasten the anchor 10 to the elongate portion 80. As shown in FIG. 3b, rotating the anchor 10 so that the longitudinal body 13 is in line with the elongate portion 80 of the stent strut can snap the curved portions 14, 18 around the stent strut, thus attaching the anchor 10 to the stent.

An anchor can be provided such that it is fastened to the elongate portion 80 by turning the anchor 10 in a counter-clockwise direction. The curved portions 14, 18 also can be provided such that the longitudinal body 13 of the anchor 10 contacts the elongate portion and then adjusted by turning about 45 degrees to fit onto the elongate portion 80.

Figure 4:
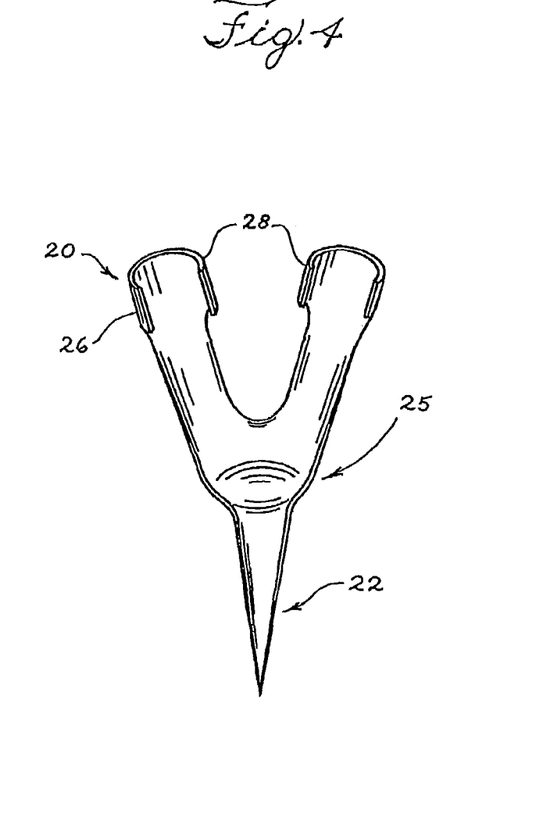
FIG. 4 is a perspective view of a monolithic anchor with a bifurcated end.

As shown in FIG. 5a, an endoluminal prosthesis can include a support structure comprising a curvilinear portion 85 having a first strut 82 and a second strut 88 meeting at an apex 83. The prosthesis also can include an anchor 20 comprising an anchor body and one or more barbs 21 extending outwardly from the anchor body. The anchor body fits at least partially about, and conforms to, the first strut 82, the second strut 88, and the apex 83. In FIG. 4, the anchor has a longitudinal structure with a first end 22 with a barb 21 and a second, bifurcated end 25. The second end 25 includes a first substantially curved clamping portion 26 configured to fit about the first strut 82 and a second substantially curved clamping portion 28 configured to fit about the second strut 88.

FIG. 5a shows a stent curvilinear portion 85 in dashed lines along with the first 82 and second 88 struts meeting at an apex 83. The apex 83 points in one direction and when an anchor 20 is attached, the barb 21 can extend in that one direction. The barb 21 also can be bent at an angle or in a different direction than the apex 83.

The second, bifurcated end 25 includes two substantially curved clamping portions 26, 28 that can be configured to fit about the two struts found on the curvilinear portion of a stent. The two substantially curved clamping portions 26, 28 can be designed for press-fit or snap-on placement onto the stent. The two substantially curved clamping portions 26, 28 also can be soldered onto the stent struts.

FIGS. 5a and 5b show the anchor 20 fastened to the curvilinear portion 85 from the front (FIG. 5a) and from a profile view (FIG. 5b). The barb 21 can contact an endoluminal wall when implanted into a vessel. The anchor 20 in FIG. 5b has a barb 21 that is bent at an angle where the barb 21 is pointing away from where the stent graft (not shown) is positioned. The barb 21 also can be in line with the apex 83 as seen in FIG. 5a or be bent laterally in a variety of directions.

An anchor can be attached to the endoluminal support structure that has a curvilinear portion with a first strut and a second strut meeting at an apex. The method of attachment can include arranging a first end of the anchor so that it fits at least partially about, and conforms to, the first strut. A second end of the anchor is arranged so that it fits at least partially about, and conforms to, the second strut. The anchor can also be arranged so that it fits at least partially about, and conforms to, the apex. The anchor can be arranged such that it is snapped to the first strut, the second strut, and the apex of the curvilinear portion of a stent.

Figures 6, 7:
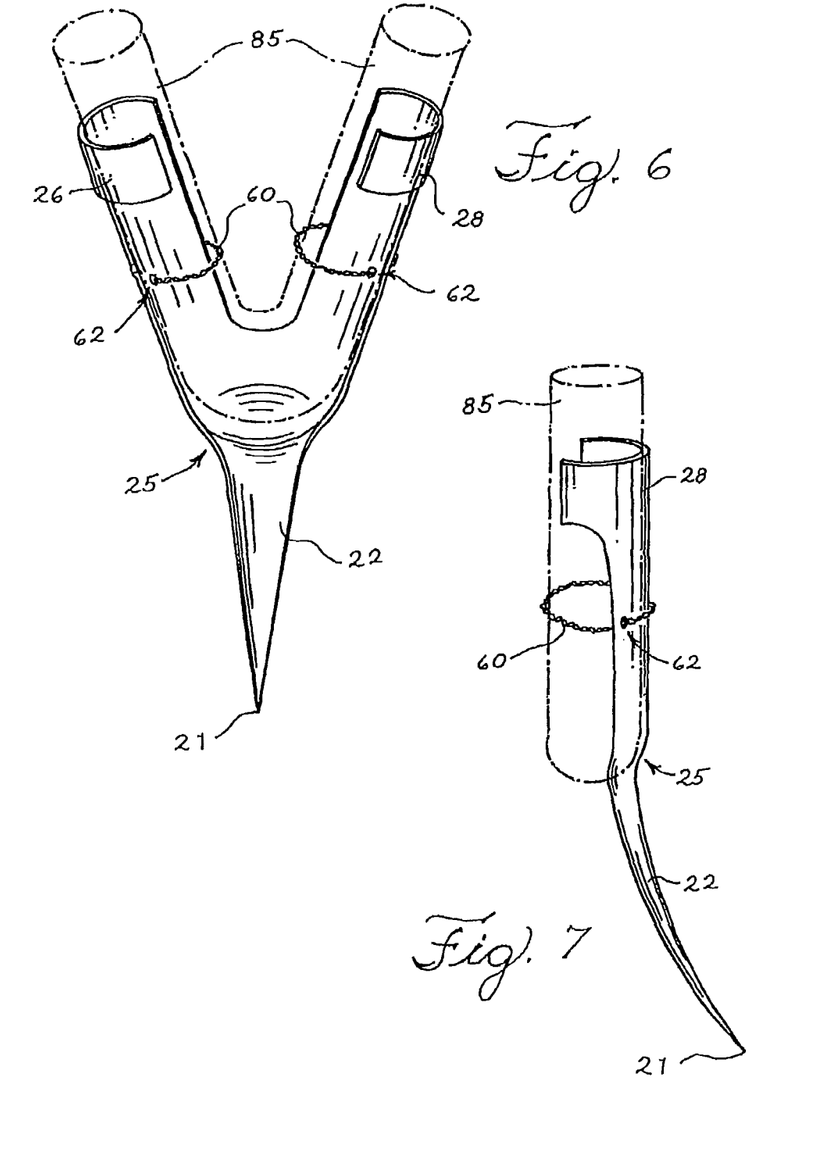
FIG. 6 is a perspective view of a monolithic anchor with a bifurcated attachment end fastened to a curvilinear portion of a stent strut with support sutures.
FIG. 7 is a profile view of an anchor fastened to a stent strut with support sutures.

Additionally, support sutures 60 can be used to fasten the anchor 20 to a stent. FIG. 6 shows an anchor 20 with a second bifurcated end 25 with openings 62 in the substantially curved clamping portions 26, 28 through which support sutures 60 can be threaded. FIG. 7 is a profile view of an anchor 20 having support sutures 60 threaded around the curvilinear portion 85, through the openings 62, and around the second curved portion 28. The support sutures 60 can be threaded at least partially around the first 26 and second 28 substantially curved clamping portion.

Figures 8A, 8B:
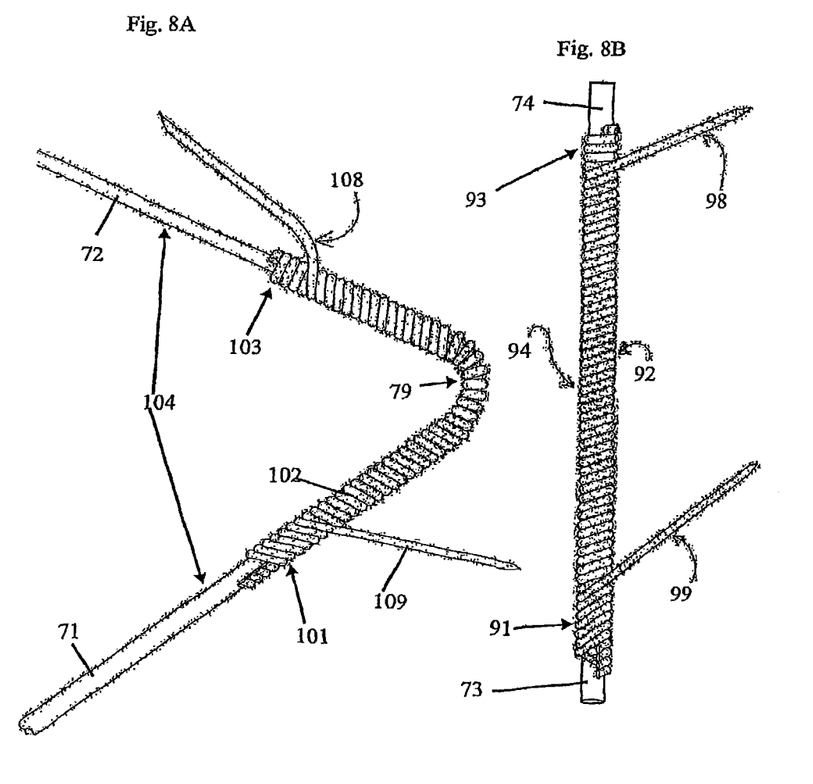
FIG. 8a is a profile view of a multi-filar anchor attached to a curvilinear stent strut.
FIG. 8b is a profile view of a multi-filar anchor attached to an elongate strut.

FIGS. 8a and 8b show anchors 102 and 92 attached to curvilinear 104 and elongate 94 stent struts. Anchors 102 and 92 are made of a plurality of independent wires arranged in a multi-filar tube having a first end, a second end, and a longitudinal axis. In multi-filar anchors, one of the wires has an end that exits the multi-filar tube and forms a first barb that extends outwardly from the anchoring device. In FIGS. 8a and 8b, the wires are coiled around stent struts 104, 94 to form the multi-filar tubes. The anchors 102, 92 resemble a coil or barbed wire configuration. The wires can have a circular cross-section or a polygonal cross-section. In FIG. 8a, the tube has a first end 101 disposed, at least in part, about the first strut 71 and a second end 103 disposed, at least in part, about the second strut 72. The tube is also disposed around the apex 79 of the curvilinear stent 104 strut. In FIG. 8b, the multi-filar anchor 92 is disposed on an elongate stent strut 94 from the first end 73 to the second end 74 of the stent. The multi-filar anchors have wires wherein each of the wires have a first end disposed at or near the first end of the multi-filar tube and a second end disposed at or near the second end of the multi-filar tube.

At least one wire in the multi-filar anchor has an end that forms at least one barb. In FIGS. 8a and 8b, the multi-filar anchors 102, 92 have barbs 108, 109, 98, 99 formed from the sharpened ends of corresponding wires. Barb 108, which extends outwardly from the anchor 102, is formed from a first wire having an end. There is also a second wire that has an end that forms a second barb 108 that extends outwardly from anchor 102. Similarly, in FIG. 8b, the anchor 92 attached to the elongate strut 94 has a first end 91 that has a barb 99 disposed thereon and a second end 93 with a barb 98 disposed thereon. It is appreciated that a multi-filar anchor similar to that shown in FIG. 8a can be attached to a Z-stent. A multi-filar anchor similar to that show in FIG. 8b can be attached to other interconnected support structures or stents.

When attaching the multi-filar anchor 102, at least a portion of the anchor can be threaded around the first strut 71, the second strut 72, and the apex 79 of the curvilinear stent 104 strut. Similarly, as shown in FIG. 8b, anchor 94 can be threaded around an elongate stent strut 94.

An anchor can be attached to the support structure in a position fixed longitudinally and rotationally. Although some incidental movement can be allowed, the anchor can be attached and fixed such that it will not move substantially longitudinally along a stent or rotate about the stent. The attachment is such that there can be little or no movement by the anchor independent of the stent structure. With monolithic anchors having bifurcated attachment ends, there can be little or no longitudinal or rotational movement. The anchor can be fastened to the stent by laser weld, adhesive, soldering, or friction fit. The anchor can also include nitinol. The substantially curved clamping portions can include nitinol. The nitinol clamping portions can be configured to constrict around a stent strut and provide a secure attachment between the anchor and the stent, which can be also found in U.S. Pat. App. Publication 2010/0057195 to Boeder et al., which is incorporated herein by reference in its entirety.

Figure 9A:
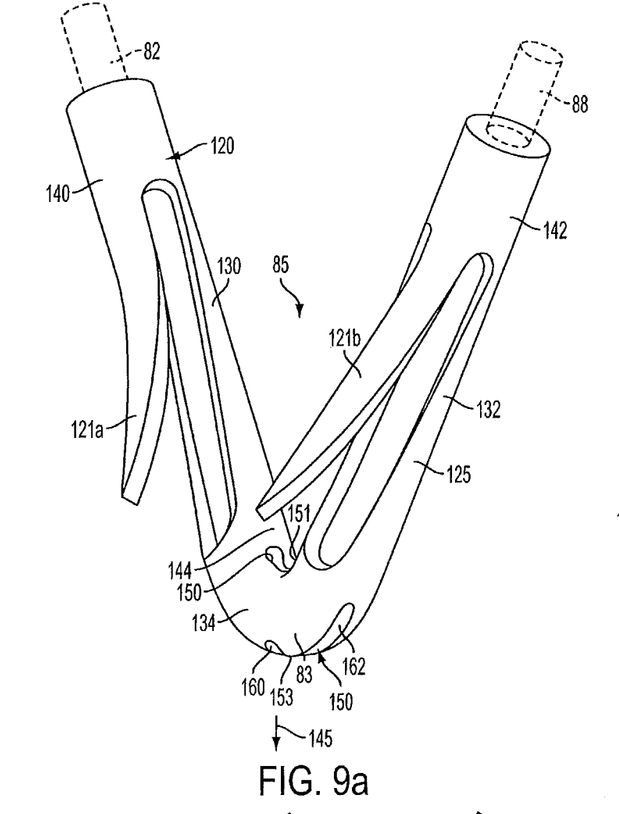
FIG. 9a is a perspective view of another example of an anchor coupled to a support structure.

As shown in FIG. 9a, an endoluminal prosthesis can include a support structure such as a zigzag stent (shown in phatom lines), which includes the curvilinear portion 85 having the first strut 82 and the second strut 88 meeting at the apex 83. The prosthesis also can include an anchor 120 with an anchor body 125 and one or more barbs (a barb 121a and a barb 121b). The barbs can extend in any direction, but preferably extend outwardly from the anchor body 125 in a manner to purchase the vessel wall, such as in an outward radial direction that is defined when the prosthesis is implanted within the body vessel. The anchor 120 can include one or more of the features described above with respect to the anchors 10, 20, 92, and 102. Other anchor configurations are described in U.S. Pat. No. 7,572,289 to Sisken et al, which is incorporated herein by reference in its entirety. The anchor body 125 can fit at least partially about, and can conform to, the first strut 82, the second strut 88, and the apex 83 such that the anchor body has a curvilinear body substantially corresponding to the curvilinear portion 85 of the stent. To this end, the anchor body 125 can include a first linear segment 130 to conform about the first strut 82, a second linear segment 132 to conform about the second strut 88, and a curved segment 134 interconnected between the first and second linear segments 130, 132 to conform about the apex 83. The anchor 120 may have geometries permitting a mechanical interference fit onto the curvilinear portion 85, preferably without the use of an additional joining mechanism. The anchor body may be configured to support the resultant forces and moments through the points of contact between the support structure and the anchor 120. The anchor body may have a different resilience than that of the support structure along the curvilinear portion 85 for further locking the anchor onto the support structure.

To further prevent the anchor body from separating from the curvilinear portion 85 of the stent, the anchor body 125 can have continuous ring portions that circumferentially surround segments of the curvilinear portion 85. In one example, a first ring 140 and a second ring 142 can be formed along the linear segments of the anchor body 125 to prevent dislodgement from the support structure. The first and second rings may be positioned at the base of the respective barbs 121a, 121b to provide structural support to the barbs. The first ring 140 can be formed at the end of the first linear segment 130, and the second ring 142 can be formed at the end of the second linear segment 132. At least one ring 144 can be positioned along the curved segment 134 of the anchor body 125 to prevent dislodgement.

Figure 9B:
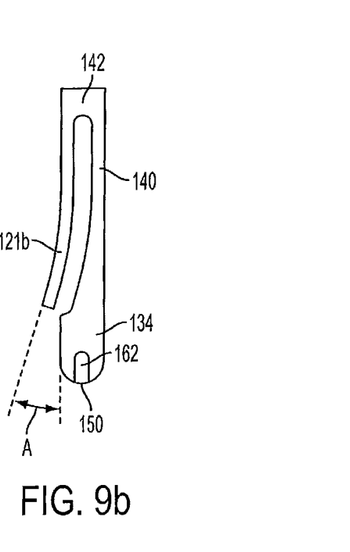
Figure 9C:
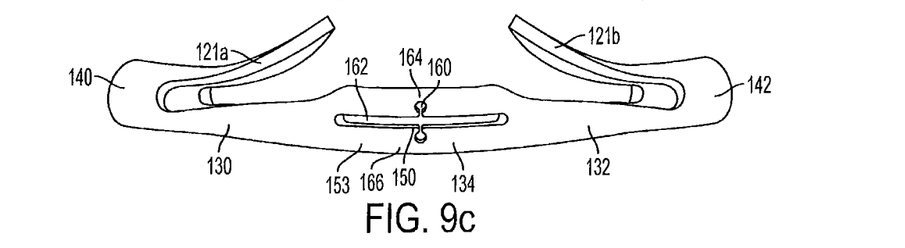

The barbs 121a, 121b can be formed in the anchor body 125 so that the anchor 120 and the barbs are formed in an integral or unitary structure. However, it is contemplated that the barbs can be discrete members attached to the anchor body. The barbs can be plastically deformed or otherwise be set into an angled configuration at an angle A relative to the axis of the body such that the barbs extend away from the anchor body to better penetrate and anchor into tissue or wall of a mating graft when the prosthesis is expanded, as shown in FIG. 9b. Angle A can be about 0 to about 90 degrees, and preferably about 10 to about 30 degrees. As shown in FIGS. 9a-9c, the apex 83 can point in a first direction 145 such as the distal direction, and when an anchor 120 is attached to the stent, the barbs 121a, 121b may also extend in the first direction 145. The barbs 121a, 121b also can be extended in any direction different from the first direction.

Relief cutouts 150 can be formed in the anchor body 125. The cutouts 150 can be of various geometric shapes to allow for material stability during plastic deformation of the anchor body 125, and may provide stress and/or strain relief. The cutouts 150 can allow for easier bending of the apex 83 of the curvilinear portion 85 during its formation and/or during use of the anchor body 125 and the support structure within the body vessel. The surfaces where the cutouts are to be located can be under excessive strain or stress due to the tensile and/or compressive forces while the apex is formed. The cutouts 150 can prevent stress risers from buckling, kinking, and/or flattening of the anchor body 125 during bending. The cutouts 150 can be placed along the inside 151 of the bending radius, the outside 153 of the bending radius, or both. The preferred size and shape of the material removed from the anchor body in forming the cutouts can be determined by one or more factors including the dimensions of the stent member to which it is attached, the size of the anchor body, the bending force, and the desired angle during formation. When the cutouts become large, the degree of interference attachment can be reduced, as well as the structural support provided by the anchor body to the barb can be reduced.

In FIGS. 9a-9c, the cutout geometry can be composed of one or more circumferential slots 160 and/or one or more lateral slots 162. The lateral slot 162 may be oriented to be substantially orthogonal to the circumferential slot 160. As shown in FIG. 9c, the lateral slot 162 can extend at least partially through the wall of the anchor body 125 for a length in a direction defined from one end of the cannula to the other end of the cannula. The circumferential slot 160 can be positioned along the apex of the curved segment when bent, for example, along the inside 151 and/or the outside 153 of the bending radius. When one circumferential slot is formed along the outside and another circumferential slot is formed along the inside of the bending radius, the circumferential slots can be circumferentially spaced from one another to define one or more connecting members 164, 166 of continuous material that interconnect the first and second linear segments 130, 132. The circumferential slot 160 may have enlarged portions removed at the ends of the circumferential slots 160, shown as circular ends, to help distribute stress during bending. When bent, the circumferential slot 160 that is along the outside 153 of the bending radius may slightly expand due to tensile forces, while the circumferential slot 160 along the inside 151 of the bending radius may slightly compress due to compressive forces.

Figure 10A:
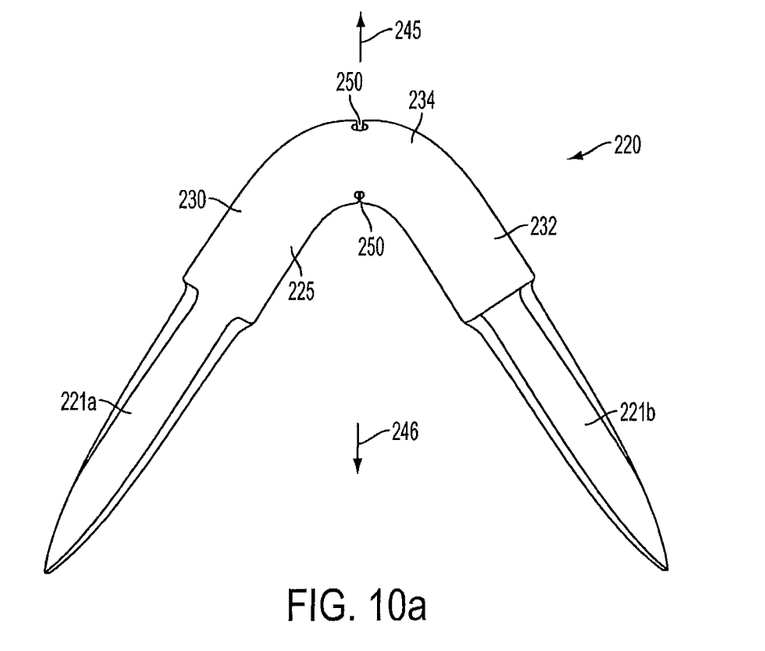
FIG. 10a is a front view of another example of an anchor.
Figure 10B:
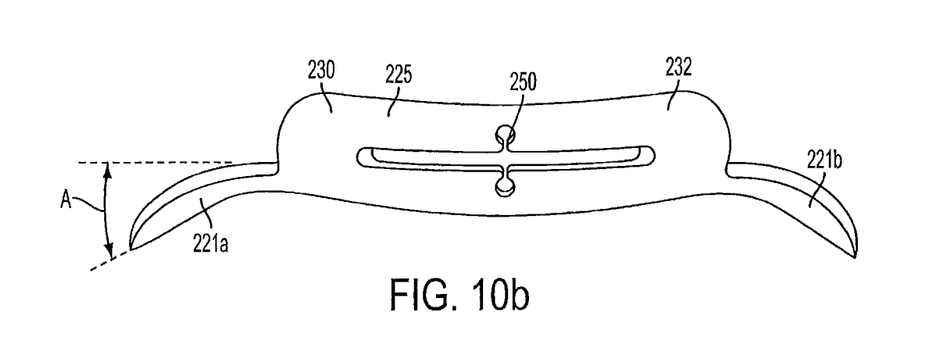

FIGS. 10a-10b depict another embodiment of an anchor 220, which can have one or more of the features of the anchor 120. The anchor body 225 can include a first linear segment 230 to conform about a first strut of the support structure, a second linear segment 232 to conform about a second strut of the support structure, and a curved segment 234 interconnected between the first and second linear segments 230, 232, to conform about an apex of the support structure. The apex can point in a second direction 245 such as the proximal direction, opposite the first direction 246, and when the anchor 220 is attached to the support structure, the barbs 221a, 221b may extend in the first direction 246. Instead of the barbs pointing inward from the ends of the anchor toward the apex as shown in the anchor 120, the barbs of the anchor 220 can point from the ends away from the apex. In FIG. 10b, the barbs 221a, 221b can extend away from the anchor body to better penetrate and anchor into tissue or mating graft when the prosthesis is expanded. The barbs can be plastically deformed or otherwise be set into an angled configuration at the angle A relative to the axis of the body. The anchor also can include a cutout 250 similar to the cutout 150 shown in FIG. 9c.

FIGS. 11a-11d depict another geometry of the cutout 260 which can be formed in the anchor 120 or 220. The cutout 260 can be composed of one or circumferential slots. As shown in the figures, three series 264a, 264b, 264c of circumferential slots 266a, 266b are shown spaced laterally from one another. Any number of circumferential slots 266a, 266b, such as, for example, one, three, four or more, may form a series, and any number of series may be used, such as, for example, one, two, four or more. One or more bridges 270 can separate the circumferential slots 266a, 266b within each series to connect one end 272 of the anchor body to the other end 274 of the anchor body. The bridge 270 can provide structural support to the anchor body. The bridge 270 can be formed along any portion of the anchor body, preferably extending laterally along the body and offset from the inside 276 and/or the outside 278 of the bending radius, for example, by about ninety degrees.

Figure 11A:
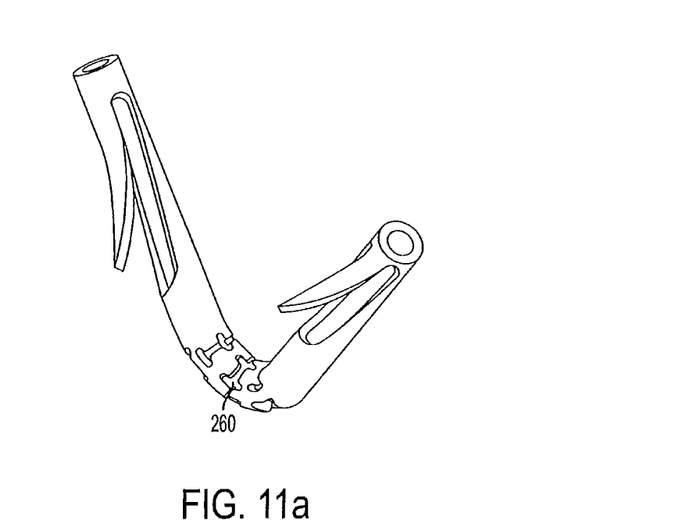
FIG. 11a is a perspective view of another anchor with a relief cutout.
Figure 11B:
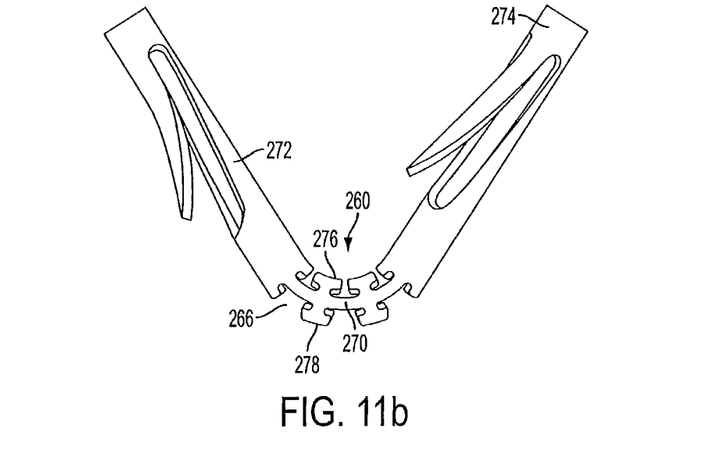
Figure 11C:
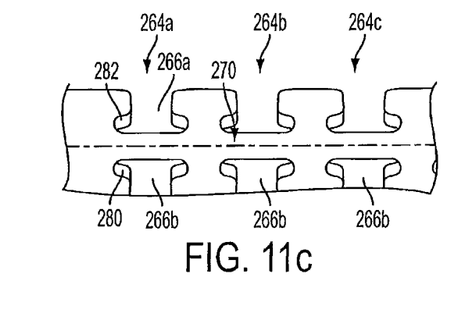
FIG. 11c is a magnified view of the relief cutout of the anchor in FIG. 11a, in a radial direction that is orthogonal to a longitudinal direction of an implanted prosthesis.
Figure 11D:
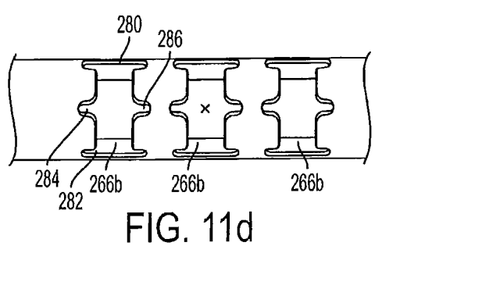
FIG. 11d is a magnified view of the relief cutout of the anchor in FIG. 11a, in a longitudinal direction of an implanted prosthesis.

In FIG. 11d, each of the circumferential slots 266a, 266b may be I-beam shaped such that the ends 280, 282 of the slot 266b extend laterally beyond the edges of a central portion 284 that connects the ends. The ends 280, 282 can be in alignment with one another and be formed along the bridge 270 to help distribute the stress during bending of the anchor. An intermediate portion 286 of the circumferential slot 266b may also laterally extend beyond the edges of the central portion 284, and preferably extend laterally by about the same distance as the ends. The intermediate portion 286 is preferably formed along the inside 276 and/or the outside 278 of the bending radius. The first series 264b of the circumferential slots 266a, 266b can be positioned directly at the apex. When the anchor is bent, the edges that define the central portion 284 of the circumferential slot 266b that is formed along the outside 278 of the bending radius may farther separate or expand due to tensile forces. The edges of the central portion 284 of the circumferential slot 266a that is formed along the inside 276 of the bending radius may be brought closer together or compress due to compressive forces. Other geometries for the cutouts are contemplated including V-shaped notches or a helical cutout portion along the curved portion of the anchor body.

Figure 12A:
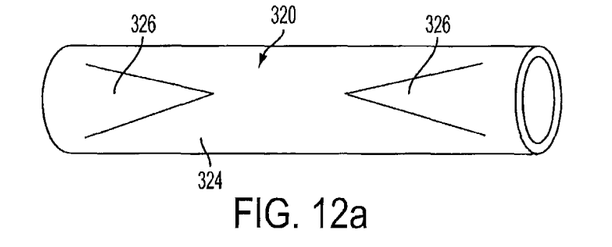
FIGS. 12a-12d are perspective views depicting a method of attaching an anchor to a support structure.

FIGS. 12a-12d depicts some of the steps for making the anchor 320 and attaching the anchor 320 to a strut 322 to form a support structure. It is contemplated that anchors 10, 20, 92,

102, 120, or 220 may be formed and attached in a similar process. In FIG. 12*a*, the anchor 320 can be formed out of a piece of cannula 324, such as 304 stainless steel, nitinol, or the other aforementioned materials. For example, any of anchors 10 or 20 can be formed in a manner, e.g., from a cannula, so that the curved clamping portions can be made into continuous ring segments. The size and material of the anchor cannula is determined by the dimensions and performance criteria of the support structure to which it is attached and the medical application. The luminal diameter of the cannula can be sized to closely fit and slide over the strut but with some resistance so that the cannula can maintained its position on the strut. For example, for a strut having an outer diameter of about 0.012 inches to about 0.022 inches, the cannula can have a longitudinal length of about 7 mm to about 12 mm; a wall thickness of about 0.002 inches to about 0.007 inches; a luminal diameter of about 0.0005 inches to about 0.001 inches greater than the outer diameter of the strut.

When the cannula is made of a superelastic alloy such as nitinol, the luminal diameter of the cannula can be smaller than the strut. In this instance, the luminal diameter of the cannula can be temporarily expanded for insertion over the strut. For example, the cannula can be cooled to a phase temperature, such as minus 40 degrees Celsius, to place the material in a martensitic state. Cooling of the cannula in this manner, in some cases, can permit expansion of the luminal diameter of up to about 10%, and preferably up to about 8%, before being warming. As a result, the chilled cannula can be slid over the strut and located at the desired bending sites along the strut. Upon warming of the anchor, the cannula will then begin contracting to its original size, thereby forming a secure interference fit along the strut.

The barb configuration 326 and/or the relief cutout configuration can then be formed in the cannula 324 with a cutting mechanism. The cutting mechanism can include laser cutting, EDM, high-pressure jet, chemical etching, machining, grinding, or stamping. As a result, the anchors and/or barbs can be produced or formed more economically and of more consistent quality than is possible with standard barb fabrication techniques that involve welding or soldering discrete wire barbs to the strut.

Figure 12B:
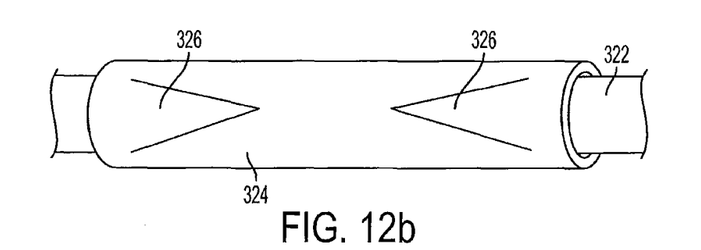

In FIG. 12*b*, after forming the barb configuration 326 and/or relief cutout configuration in the cannula 324, the strut 322 can be inserted through the lumen of the cannulas 324. The cannula 324 can be translated over the strut 322 to a bending site along the strut where the apex of the curvilinear portion of the strut will be formed. In some instances, the bending site can be where the distal apex, the proximal apex, or both will be located. Preferably, the middle of the cannula is placed directly over the portion of the strut where the apex is to be formed. The size relationship between the cannula and the strut is such that there can be enough friction to effectively maintain the cannula at a fixed position along the strut without an additional joining mechanism. However, a temporary or permanent joining mechanism can be used to secure the cannula to the strut before bending into zigzag or serpentine configuration.

Figure 12C:
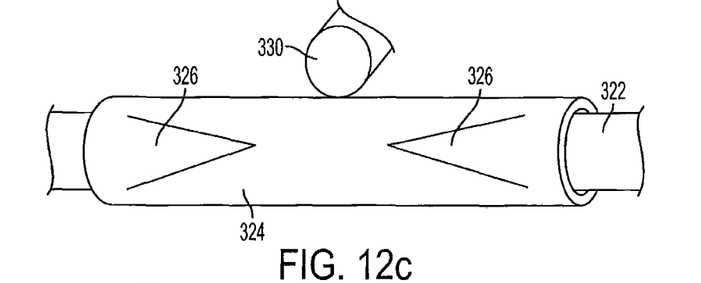
Figure 12D:
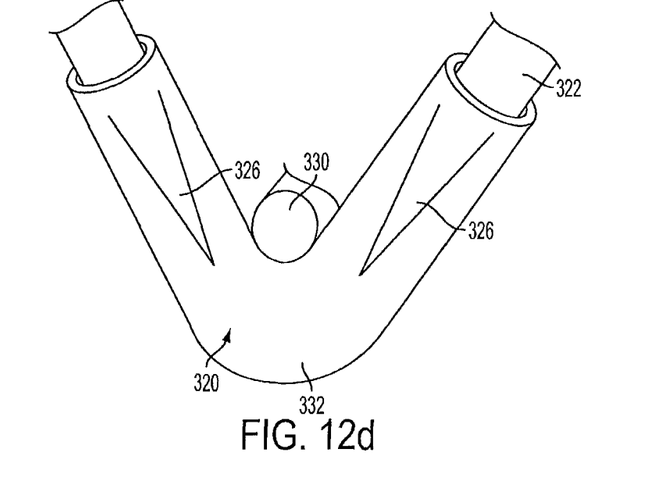
Figure 13A:
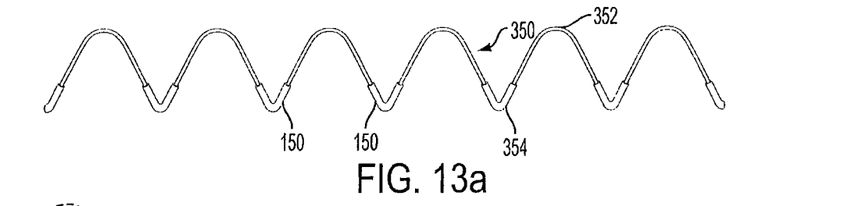
FIG. 13a is a front view depicting anchors coupled to a zigzag support structure.
Figure 13B:
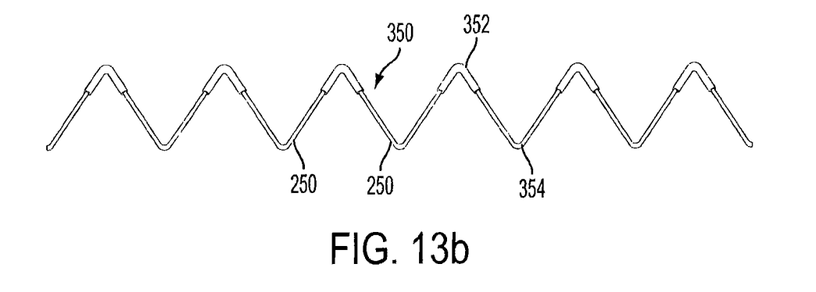
FIG. 13b is a front view depicting anchors coupled to a zigzag support structure.

In FIG. 12*c*, the strut 322 with the cannula 324 can be positioned at a bending mechanism having a fixed bending mandrel 330, which can be found in a stent-bending machine or on a building block where the bends can be formed manually. In FIG. 12*d*, a sufficient force can be applied to the strut 322 and the cannula 324 for bending about the fixed bending mandrel 330 to form a portion of a support structure having a zigzag or serpentine configuration. For example, FIGS. 13*a-b* depict a support structure 350 in a zigzag configuration having proximal apices 352 and distal apices 354. In FIG. 13*a*, a series of anchors 150 can be coupled to distal apices 354 of the support structure 350, while in FIG. 13*b*, a series of anchors 250 can be coupled to proximal apices 352 of the support structure 350. It may be desirable to place the anchors only along one set of apices, such as the proximal apices, or to alternate between apices, such as distal and proximal apices, thereby leaving some of the apices uncovered by the anchors in order to increase flexibility. During the bending process, the strut 322 and the cannula 324 can be bent together such that the apex of the support structure and the curved portion 332 of the anchor 320 are formed simultaneously.

The anchor 320 can be directly coupled to the apex of the strut 322 with a mechanical interference fit. Preferably, the anchor is coupled to the strut without spot welding, laser welding, crimping, adhesive bonding, or other joining mechanisms, which can cause stress risers that alter the long-term durability of the stent and/or increase the risk of premature loosening or breaking of a bond if not controlled properly. To this end, the formation of a support structure with anchors can be achieved more rapidly without the additional process time and materials associated with the aforementioned joining mechanisms. However, it may be helpful to utilize the aforementioned joining mechanisms to help secure the anchor to the strut. For example, as describe above a temporary joining mechanism may be used to temporality fix the cannula to the strut before the bending process. A frangible bond may be used to hold the cannula in place before bending, but such frangible bond can be broken during the bending process. In one example, two tack welds can be formed on either side of the bend. The tack welds are sufficient to hold the cannula in place before bending, but during bending tension can break the tack welds.

The barbs 326 formed into the cannula 324 can be oriented to a desired position for purchasing the vessel wall or mating into a stent graft, such as shown in FIGS. 9*a* and 10*b*. In one example, the barbs 326 can be plastically deformed manually into the desired configuration as described herein. For instance, a loop of a wire can be inserted around the barb, and slid toward the base of the barb to urge the barb to pivot outward away from the anchor body. Other methods of forming barbs, as well as other barb configurations, can be found in previously incorporated U.S. Pat. No. 7,572,289 to Sisken et al. It is contemplated that when the cannula is made of a superelastic alloy such as nitinol, the cannula can be thermally processed in a manner so that during the formation of the curved portion of the anchor, the barb assumes the desired configuration by pivoting outward from its base.

It is contemplated that the anchor 20 can be configured in a first configuration prior to being bent to a bent configuration shown in FIG. 5*a*. For example, the anchor 20 may be substantially linear such that the strut of the support structure, which is in a first configuration prior to bending, can be inserted within the lumen formed by the curved clamping portions. After insertion, the anchor 20 and the strut can be bent together to result in the bent configuration. Further, the anchor 102 can be configured in a first configuration, similar to what is shown in FIG. 8*b*, prior to being bent to a bent configuration shown in FIG. 8*a*. For example, the multi-filar tube of the anchor 102 may be substantially linear such that the strut of the support structure, which is in a first configuration prior to bending, can be inserted within the lumen of the multi-filar tube. Optionally, the multi-filar tube can be coiled around the strut in the first configuration. The anchor 102 and the strut can be bent together to result in the bent configuration.

Drawings in the figures illustrating various embodiments are not necessarily to scale. Some drawings may have certain details magnified for emphasis, and any different numbers or proportions of parts should not be read as limiting, unless so-designated in the present disclosure. Those skilled in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

What is claimed is:

1. An endoluminal prosthesis comprising:
   a support structure comprising a curvilinear portion having a first straight section, a second straight section, and an apex between the first and second straight sections; and
   an anchor comprising a tubular body;
   where the tubular body has a first segment configured to fit about the first straight section, a second segment configured to fit about the second straight section, and a third curved segment to fit about and conform to a curvature of the apex;
   where the first segment of the tubular body comprises a first continuous circumferential ring segment, and the second segment of the tubular body comprises a second continuous circumferential ring segment;
   where at least one of the first segment or second segment comprises an integral barb extending therefrom.

2. The prosthesis of claim 1, where the apex points in a first direction and the one or more barbs extend toward a second direction, different from the first direction.

3. The prosthesis of claim 1, where the one or more barbs extend at an angle away from the tubular body.

4. The prosthesis of claim 1, where the one or more barbs comprise a first barb and a second barb, the first barb extending from the first ring segment toward the apex, the second barb extending from the second ring segment toward the apex.

5. The prosthesis of claim 1, where a first barb of the one or more barbs extends from the tubular body in a direction away from the apex.

6. The prosthesis of claim 1, where the anchor body comprises one or more relief cutout portions formed along the third curved segment.

7. The prosthesis of claim 6, where the one or more relief cutout portions comprise two circumferential slots spaced from one another to define a first bridge and a second bridge, the first bridge and the second bridge connecting the first and second segments of the tubular body.

8. The prosthesis of claim 7, where one of the circumferential slots is formed along an inner bending radius portion of the third curved segment, and the other of the circumferential slots is formed along an outer bending radius portion of the third curved segment.

9. The prosthesis of claim 8, where the first and second bridges are disposed circumferentially offset from the location of the inner and outer bending radius portions.

10. The prosthesis of claim 6, where the third curved segment comprises an inner bending radius portion and an outer bending radius portion, the one or more relief cutout portions further comprise a lateral extending slot disposed along at least one of the inner and the outer bending radius portions of the third curved segment.

11. The prosthesis of claim 1, where at least one of the first segment or second segment comprises a coil.

12. An endoluminal prosthesis comprising:
    a stent comprising a curvilinear portion, the curvilinear portion having a first strut and a second strut meeting at an apex; and
    a tubular anchor comprising a first segment configured to fit over the first strut, a second segment configured to fit over the second strut, and a third segment between the first and second segments, wherein the third segment is conformed to fit about the apex of the curvilinear portion of the stent;
    wherein the tubular anchor further comprises one or more barbs extending from the tubular anchor, and one or more relief cutout portions formed along a curvature of the third segment.

13. The prosthesis of claim 12, where the tubular anchor is coupled to the stent with a mechanical interference fit.

14. The prosthesis of claim 12 formed by the process comprising:
    simultaneously bending a strut member of the stent and a tubular body of the anchor together at a bending site so that the curvature of the curvilinear portion of the stent and the third segment of the tubular anchor are formed together.

* * * * *